(12) United States Patent
Chan et al.

(10) Patent No.: US 9,931,457 B2
(45) Date of Patent: Apr. 3, 2018

(54) COMPOSITIONS AND METHODS USEFUL IN SELECTIVELY MODIFYING THE INTERNAL AND EXTERNAL SURFACES OF POROUS POLYMER BEADS

(75) Inventors: Phillip P. Chan, Cherry Hill, NJ (US); Vincent J. Capponi, Monmouth Junction, NJ (US); Thomas D. Golobish, Princeton, NJ (US); Humayra Begum Ali, Princeton, NJ (US)

(73) Assignee: CytoSorbents Corporation, Monmouth Junction, NJ (US)

( * ) Notice: Subject to any disclaimer, the term of this patent is extended or adjusted under 35 U.S.C. 154(b) by 1130 days.

(21) Appl. No.: 13/978,218

(22) PCT Filed: Jan. 6, 2012

(86) PCT No.: PCT/US2012/020441
§ 371 (c)(1),
(2), (4) Date: Sep. 18, 2013

(87) PCT Pub. No.: WO2012/094571
PCT Pub. Date: Jul. 12, 2012

(65) Prior Publication Data
US 2014/0042097 A1    Feb. 13, 2014

Related U.S. Application Data

(60) Provisional application No. 61/430,389, filed on Jan. 6, 2011.

(51) Int. Cl.
*A61M 1/36* (2006.01)
*C08F 8/00* (2006.01)
(Continued)

(52) U.S. Cl.
CPC .......... *A61M 1/3679* (2013.01); *B01J 20/267* (2013.01); *B01J 20/28019* (2013.01);
(Continued)

(58) Field of Classification Search
None
See application file for complete search history.

(56) References Cited

U.S. PATENT DOCUMENTS 4,224,415 A    9/1980  Meitzner
4,263,407 A    4/1981  Reed, Jr.
(Continued)

FOREIGN PATENT DOCUMENTS

EP    1 291 080      3/2003
JP    2002/057934    3/2002
(Continued)

OTHER PUBLICATIONS

Davankov et al, "Macronet Isoporous Gels Through Crosslinking of Dissolved Polystyrene", Journal of Polymer Science, Polymer Symposia, 1974, 47(1), 95-101, published online Mar. 8, 2007.
(Continued)

*Primary Examiner* — Erma C Cameron
(74) *Attorney, Agent, or Firm* — Baker & Hostetler LLP

(57) ABSTRACT

The invention concerns polymer systems comprising at least one polymer with a plurality of pores where the polymer is initially functionalized on substantially all surfaces followed by a stepwise surface specific functionalization such that a different functional group resides on the external or internal pore surface of the bead. The invention also concerns use of such polymer systems in blood, blood product, or physiologic fluid purification.

26 Claims, 6 Drawing Sheets

(51) Int. Cl.
   *B01J 20/26*     (2006.01)
   *B01J 20/32*     (2006.01)
   *B01J 20/28*     (2006.01)

(52) U.S. Cl.
   CPC ....... *B01J 20/3208* (2013.01); *B01J 20/3248* (2013.01); *B01J 20/3285* (2013.01); *C08F 8/00* (2013.01)

(56) References Cited

U.S. PATENT DOCUMENTS

| | | | |
|---|---|---|---|
| 4,297,220 | A | 10/1981 | Meitzner |
| 5,627,217 | A | 5/1997 | Rifling |
| 5,904,663 | A * | 5/1999 | Braverman ......... A61M 1/3679 502/402 |
| 6,114,466 | A * | 9/2000 | Davankov ............. B01D 15/00 521/54 |
| 2004/0202783 | A1 | 10/2004 | Baumann |
| 2008/0119576 | A1* | 5/2008 | Young ................... B01J 20/261 521/29 |
| 2008/0138434 | A1* | 6/2008 | Brady ................ A61M 1/3679 424/529 |

FOREIGN PATENT DOCUMENTS

| | | |
|---|---|---|
| WO | WO 98/58734 | 12/1998 |
| WO | WO 2003/024587 | 3/2003 |
| WO | WO 2012/094571 A1 | 7/2012 |

OTHER PUBLICATIONS

Albright, "Porous polymers as an anchor for catalysis", Reactive Polymers, Ion Exchangers, Sorbents, Apr. 1986, 4(2), 155-174.

Fritz, J. "Methods and Materials for Solid-Phase Extraction", Chromatography, Feb. 1995, 691(1-2), 133-140.

Boudenne, "Modification of poly(styrene-co-divinylbenzene) Resin by Grafting on an Aluminium Selective Ligand", Polymer International, Oct. 2002, 51(10),1050-1057.

Hubbard, "The Preparation and Characteristics of Poly(divinylbenzene-co-ethylvinylbenzene), including Ambeflite XAD-4. Styrenic resins with Pendant Vinylbenzene Groups", Polymers, Feb. 1998, 36(1), 17-30.

Mercier et al, "Preparation and Functionalization of (vinyl) Polystyrene Polyhipe-Short Routes to Binding Functional Groups Through a Dimethylene Spacer", Reactive and Functional Polymers, Nov. 2000, 46(1), 67-79.

* cited by examiner

Protecting Solvent n = 9–10

Triton X-100

COMPOSITIONS AND METHODS USEFUL IN SELECTIVELY MODIFYING THE INTERNAL AND EXTERNAL SURFACES OF POROUS POLYMER BEADS

RELATED APPLICATIONS

CROSS-REFERENCE TO RELATED APPLICATIONS

This application is the national stage of PCT/US2012/020441, filed Jan. 6, 2012, which claims the benefit of priority to U.S. Provisional Patent Application No. 61/430,389, filed Jan. 6, 2011, the disclosures of which are incorporated herein by reference in their entireties.

TECHNICAL FIELD

The present invention concerns compositions and methods useful in selectively modifying the internal and external surfaces of porous polymer beads used in blood, blood product or physiologic fluid purification. This methodology is useful in preserving or imparting hemocompatibility while allowing enhanced binding (or destruction) of proteins, toxins and pathogens.

BACKGROUND

Techniques of blood purification via extracorporeal therapy or transfusion related products are reliant on the hemocompatibility of materials used. CytoSorbents has been developing porous polymers for the removal of drugs and proteins for about 11 years. The development of biocompatible, highly porous polymer beads that can remove substances from blood and physiologic fluids is the core technology. Its flagship product is CytoSorb™, a highly efficient porous bead-based cytokine filter currently in human clinical trials to treat cytokine storm in patients with sepsis and severe lung injury. Blood is pumped out of the body, directly through a CytoSorb hemoperfusion cartridge where the beads remove cytokines broadly, and the purified blood is then pumped back into the body. CytoSorb has been used safely in more than 600 human blood treatments. The polymer beads have passed strict ISO 10993 biocompatibility and hemocompatibility testing, which also includes genotoxicity, acute sensitivity, cytotoxicity and others.

Most commercial porous resins are synthesized either by macroreticular synthesis (Meitzner, et al., U.S. Pat. No. 4,224,415; 1980), such as Amberlite XAD-4® and Amberlite XAD-16® by Rohm and Haas Company or by hypercrosslinking synthesis [Davankov, et al. J. Polymer Science, Symposium No. 47, 95-101 (1974)], used to make the Hpersol-Macronet® resins by Purolite Corp. Many conventional polymeric sorbents have a large pore surface and sorbtion capacity but are not hemocompatible and therefore are not suitable for sorbtion of proteins directly from body fluids.

The porous polymeric sorbents specified in the present invention demonstrate compositions and methods useful in selectively modifying the internal and external surfaces of porous polymer beads used in blood, blood product, or physiologic fluid purification. This methodology is useful in preserving or imparting hemocompatibility while allowing enhanced binding (or destruction) of protein toxins and pathogens.

SUMMARY

In some aspects, the invention concerns polymer systems comprising at least one polymer, the polymer comprising residues of one or more aromatic monomers and one or more cross-linking agents, the polymer having an external surface and a plurality of pores, the polymer being functionalized with different functional groups on the external surface and on surfaces within the pores.

Certain aspects of the invention concern methods of functionalizing a polymer where the methods comprise (a) functionalizing the polymer on substantially all surfaces; and (b) functionalizing in a stepwise manner such that a different functional group resides on the external surface and the internal pore surface of the polymer.

Some aspects of the invention concern methods of functionalizing a polymer, the polymer comprising a plurality of pores, the pores having external and internal surfaces, the method comprising functionalizing the external surfaces such that functional groups reside on the external pore surfaces.

The invention also concerns methods of functionalizing a polymer, where the polymer comprises a plurality of pores, the pores having external and internal surfaces, the method comprising selectively functionalizing the polymer such that the functional groups reside on the internal pore surfaces.

In some embodiments, the functional groups are selected from aldehyde, carboxylic acid, ether, ester, aromatic, alkyl aromatics, alkyl, wherein said aromatic alkyl aromatic, and alkyl groups may optionally be substituted with aldehyde, carboxylic acid, alkyl, aromatic, halogen, ester or ether.

The porous polymers of this invention are constructed from aromatic monomers of styrene and ethylvinylbenzene with crosslinking provided by one of the following or mixtures of the following of divinylbenzene, trivinylcyclohexane, trimethylolpropane triacrylate and trimethylolpropane trimethacrylate. Other crosslinking agents that may be used to construct the porous polymeric sorbents of this invention are divinylnaphthalene, trivinylbenzene and divinylsulfone and mixtures thereof.

In another embodiment, the polymer sorber is synthesized by an organic solution in which 25 mole % to 90 mole % of the monomer is crosslinking agents such as divinylbenzene and trivinylbenzene, and the resulting polymer sorber has a sufficient structural strength.

The porous polymers of this invention are made by suspension polymerization in a formulated aqueous phase with free radical initiation in the presence of aqueous phase dispersants that are selected to provide a biocompatible and a hemocompatible exterior surface to the formed polymer beads. The beads are made porous by the macroreticular synthesis with an appropriately selected porogen (precipitant) and an appropriate time-temperature profile for the polymerization in order to develop the proper pore structure.

Porous beads are also made with small pore sizes by the hypercrosslinking methodology which is also known as macronetting or the macronet synthesis. In this methodology, a lightly crosslinked gel polymer—crosslinking usually less than two (2) wt. %—is swelled in a good difunctional swelling agent for the polymeric matrix. In the swollen state, the polymeric matrix is crosslinked by a catalyzed reaction. The catalyzed reaction is most often a Friedel-Crafts reaction catalyzed by a Lewis-acid catalyst. The resulting product is a porous polymer which is a crosslinked polymer having a permanent pore structure in a dry, non-swollen state.

For the purposes of this invention, the term "biocompatible" is defined as a condition of compatibility with physiologic fluids without producing unacceptable clinical changes within the physiologic fluids. The term "hemocompatible" is defined as a condition whereby a material when placed in contact with whole blood or blood plasma results in clinically acceptable physiologic changes.

In one embodiment, the present invention provides for a polymer system comprising at least one polymer with a plurality of pores, said polymer is initially functionalized on all surfaces via lewis acid, lewis base, free radical or oxidation/reduction reactions. Where the external functional groups X are selectively changed by first treating with a non-reactive organic solvent and said solvent is sorbed in the pores. The interstitial solvent is removed leaving the non-reactive organic solvent in the pores followed by suspension in an aqueous solution and external surfaces modified through lewis acid, lewis base, free radical or oxidation/reduction reactions that favor aqueous solvents leaving the internal surfaces with the initial modification X and the external Y.

In another embodiment, the present invention provides for a polymer system comprising at least one polymer with a plurality of pores, said polymer is initially functionalized on all surfaces via lewis acid, lewis base, free radical or oxidation/reduction reactions, therefore, yielding X' on all surfaces. Then where the internal functional groups are selectively changed by first sorbing aqueous solutions containing lewis acid, lewis base, free radical or oxidation/reduction reactions (Y' generating) that favor aqueous solvents followed by suspension in non-reactive organic solvent. The non-reactive organic solution protects the external surfaces with the initial modification, leaving X' on the external surface and Y' on the interior surfaces.

In still another embodiment, the present invention provides for a polymer system comprising at least one polymer with a plurality of pores, said polymer is initially functionalized on all surfaces via lewis acid, lewis base, free radical or oxidation/reduction reactions, therefore, yielding X" on all surfaces. Then where the external functional groups are selectively changed by first treating with an aqueous solution and said aqueous solution is sorbed in the pores. The interstitial solution is removed leaving the aqueous solution in the pores followed by suspension in a reactive organic solvent mix containing lewis acid, lewis base, free radical or oxidation/reduction reactions (Y" generating) that favor organic solvents leaving the internal surfaces with the initial modification X" and Y" externally.

In another further embodiment, the present invention provides for a polymer system comprising at least one polymer with a plurality of pores, said polymer is initially functionalized on all surfaces via lewis acid, lewis base, free radical or oxidation/reduction reactions X'''. Where the internal functional groups are selectively changed by sorbing a reactive organic solvent mix containing lewis acid, lewis base, free radical or oxidation/reduction reactions (Y''' generating) that favor organic solvents into the pores. The interstitial solution is removed leaving the reactive organic solvent mix in the pores followed by suspension in an aqueous solution leaving the external surfaces with the initial modification X''' and the interior functionalized with Y'''.

In yet a further embodiment, the present invention provides for a polymer system comprising at least one polymer with a plurality of pores where the porous polymer is first selectively modified on the external surface by first treating with an aqueous solution and said water is sorbed into the pores. The interstitial water is removed leaving the aqueous solution in the pores followed by suspension in an organic solvent and external surfaces modified (Z) through lewis acid, lewis base, free radical or oxidation/reduction reactions that favor organic solvents.

In still yet a further embodiment, the present invention provides for a polymer system comprising at least one polymer with a plurality of pores where the porous polymer is first selectively modified on the external surface by first treating with a non-reactive organic solvent and said non-reactive organic solvent is sorbed into the pores. The interstitial non-reactive organic solvent is removed leaving the non-reactive organic solvent solution in the pores followed by suspension in a reactive aqueous solution and external surfaces modified (Z') through lewis acid, lewis base, free radical or oxidation/reduction reactions that favor aqueous solvents.

In another embodiment, the present invention provides for a polymer system comprising at least one polymer with a plurality of pores where the porous polymer is selectively modified on the internal surface (Z") by first treating with reactive organic solvent mix containing lewis acid, lewis base, free radical or oxidation reduction agents that favor reactions in organic solvents and said solvent is sorbed in the pores. The interstitial solvent is removed leaving the reactive organic solvent mix in the pores followed by suspension in an aqueous solution to protect the external surface.

In yet another embodiment, the present invention provides for a polymer system comprising at least one polymer with a plurality of pores where the porous polymer is selectively modified (Z''') on the internal surface by first treating with an aqueous solution containing lewis acid, lewis base, free radical or oxidation reduction agents that favor reactions in aqueous solvents. The interstitial solvent is removed leaving the reactive aqueous solution in the pores. The external surface is protected by suspension in a non-reactive organic solvent.

In one embodiment, the present invention provides for a polymer system comprising at least one polymer with a plurality of pores, said polymer is initially functionalized on all surfaces via lewis acid, lewis base, free radical or oxidation/reduction reactions. Where the external functional groups X are selectively changed by first purging the dry polymer with a non-reactive gas such as, air, nitrogen, argon. Then the gas saturated polymer beads are suspended in an aqueous solution and the external surfaces are modified through lewis acid, lewis base, free radical or oxidation/reduction reactions that favor aqueous solvents leaving the internal surfaces with the initial modification X"" and the external with the modification Y"".

In still yet a further embodiment, the present invention provides for a polymer system comprising at least one polymer with a plurality of pores where the porous polymer is first selectively modified on the external surface by first purging the dry polymer with a non-reactive gas such as air, nitrogen, argon to name a few. Then the gas saturated polymer beads are suspended in an aqueous solution and the external surfaces are modified (Z"") through lewis acid, lewis base, free radical or oxidation/reduction reactions that favor aqueous solvents.

Depending on the functionality these embodiments allow for repeated protection and de-protection of polymer surfaces, therefore, allowing flexibility in functionalization. Some embodiments, after selective surface modification can be further derivatized without a protection/deprotection scheme based on the already fixed functionality.

In these embodiments, solvent or aqueous solvent organic maybe viscosified to improve retention in the polymer pores.

For the purposes of this invention, the term "macroreticular synthesis" is defined as a polymerization of monomers into polymer in the presence of an inert precipitant which forces the growing polymer molecules out of the monomer liquid at a certain molecular size dictated by the phase equilibria to give solid nanosized microgel particles of spherical or almost spherical symmetry packed together to give a bead with physical pores of an open cell structure [U.S. Pat. No. 4,297,220, Meitzner and Oline, Oct. 27, 1981; R. L. Albright, Reactive Polymers, 4, 155-174 (1986)]. For purposes of this invention, the term "sorb" is defined as "taking up and binding by absorption and adsorption".

XPS data is quantified using relative sensitivity factors and a model that assumes a homogeneous layer. The analysis volume is the product of the analysis area (spot size or aperture size) and the depth of information. Photoelectrons are generated within the X-ray penetration depth (typically many microns), but only the photoelectrons within the top three photoelectron escape depths are detected. Escape depths are on the order of 15-35 Å, which leads to an analysis depth of ~50-100 Å. Typically, 95% of the signal originates from within this depth. When a sample analyzed is considered for the External Surface, the whole beads or as received is analyzed. When one considers the Internal Surface the sample is ground. Atomic Concentrations are recorded in % and are normalized to 100% of the elements detected. XPS does not detect H or He.

Also for purposes of this invention, the terms Lewis acid/Lewis base chemistry refer to a Lewis base is a chemical species with an available (reactive) pair of electrons and a Lewis acid is an electron pair acceptor.

For the sake of clarity, some of the preceding embodiments have been tabulated in Table 1 & 2.

FIG. 9 illustrates an example of use of lipophilic and lipophobic polymer cores and biphasic conditions to exploit free radical grafting on the interior and exterior of the polymer bead which can be augmented by the selection of organic soluble and water soluble free radical initiators.

FIG. 10 graphical data of selective free radical grafting of styrenesulfonic acid sodium salt.

DETAILED DESCRIPTION OF ILLUSTRATIVE EMBODIMENTS

As required, detailed embodiments of the present invention are disclosed herein; it is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the invention to be better understood. However, they are given merely by way of guidance and do not imply any limitation.

Some solutions used in the methods described herein can be viscosified to assist maintaining the fluids within pores during process steps. Viscosification is well known to those skilled in the art and can be accomplished, for example, by dissolving a polymer in the solvent to increase viscosity.

With hydrophobic polymer compositions, the polymer may need to be wetted to assist in inclusion of aqueous

TABLE 1

| ¶ No. | Initial Function alization | Reactive Organic | Reactive Aqueous | Protective Organic | Protective Aqueous | External Function alization | Internal Function alization |
|---|---|---|---|---|---|---|---|
| 0011 | Yes | — | External | Internal | — | Y | X |
| 0012 | Yes | — | Internal | External | — | X' | Y' |
| 0013 | Yes | External | — | — | Internal | Y'' | X'' |
| 0014 | Yes | Internal | — | — | External | X''' | Y''' |
| 0015 | No | External | — | — | Internal | Z | — |
| 0016 | No | — | External | Internal | — | Z' | — |
| 0017 | No | Internal | — | — | External | — | Z'' |
| 0018 | No | — | Internal | External | — | — | Z''' |

TABLE 2

| ¶ No. | Initial Functionali- zation | Reactive Aqueous | Protective Gas | External Functionali- zation | Internal Functionali- zation |
|---|---|---|---|---|---|
| 0019 | Yes | External | Internal | Y'''' | X'''' |
| 0020 | No | External | Internal | Z'''' | — |

solutions within the pores. Wetting techniques are well known to those skilled in the art.

EXAMPLES

Example 1

Sorbent Syntheses

Figure 1:
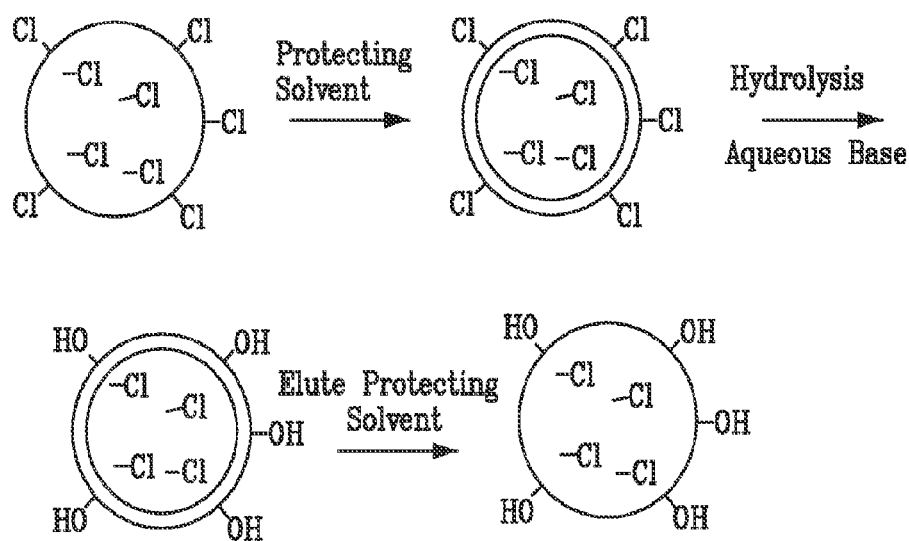
FIG. 1 illustrates the concept of protecting solvent.

The present invention provides for a porous polymer to be protected inside the pore surface with a non-reactive organic solvent (toluene, hexane, etc.) while cleaving the exterior reactive functionality under neutral, acidic or basic aqueous conditions. The organic protecting phase could be thickened with a straight chain polymer to insure adhesion to the bead interior. This protecting phase can be eluted at will. This concept is diagramed in FIG. 1.

Figure 2:
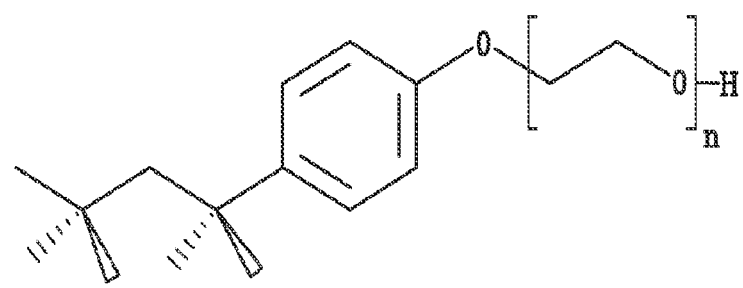
FIG. 2 presents the structure of Triton X-100.
Figure 3:
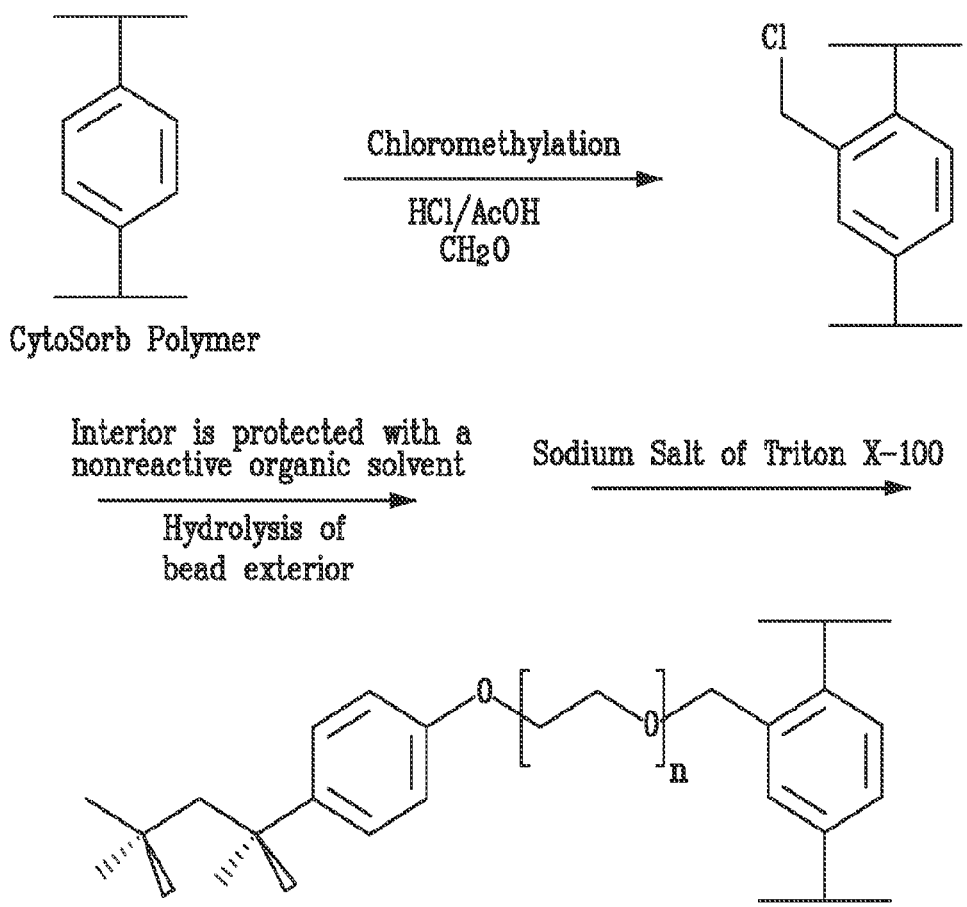
FIGS. 3 and 4 represent selectively reacting the inner core with Triton X 100 to leave the exterior hemocompatible.
Figure 4:
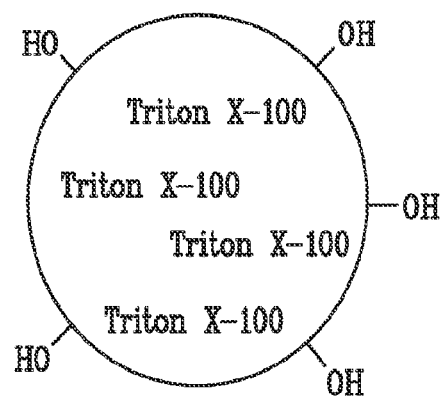

In this example we would then selectively react the inner core with Triton X 100 (FIG. 2) leaving, the exterior hemocompatible FIGS. 3 & 4.

CytoSorb polymer is chloromethylated (J. S. Fritz et al., J. Chromatography. A 691, (1995) 133-140) and then treated with toluene. The interstitial liquid (between the beads) is removed and replaced with an aqueous phase to convert the reactive exterior chloromethyls to hydroxymethyls. The protecting solvent is eluted via column chromatography or a Soxhlet apparatus. Further reaction with the sodium salt of Triton X-100 modifies only the interior pore surface leaving the exterior of the bead hemocompatible.

Figure 5:
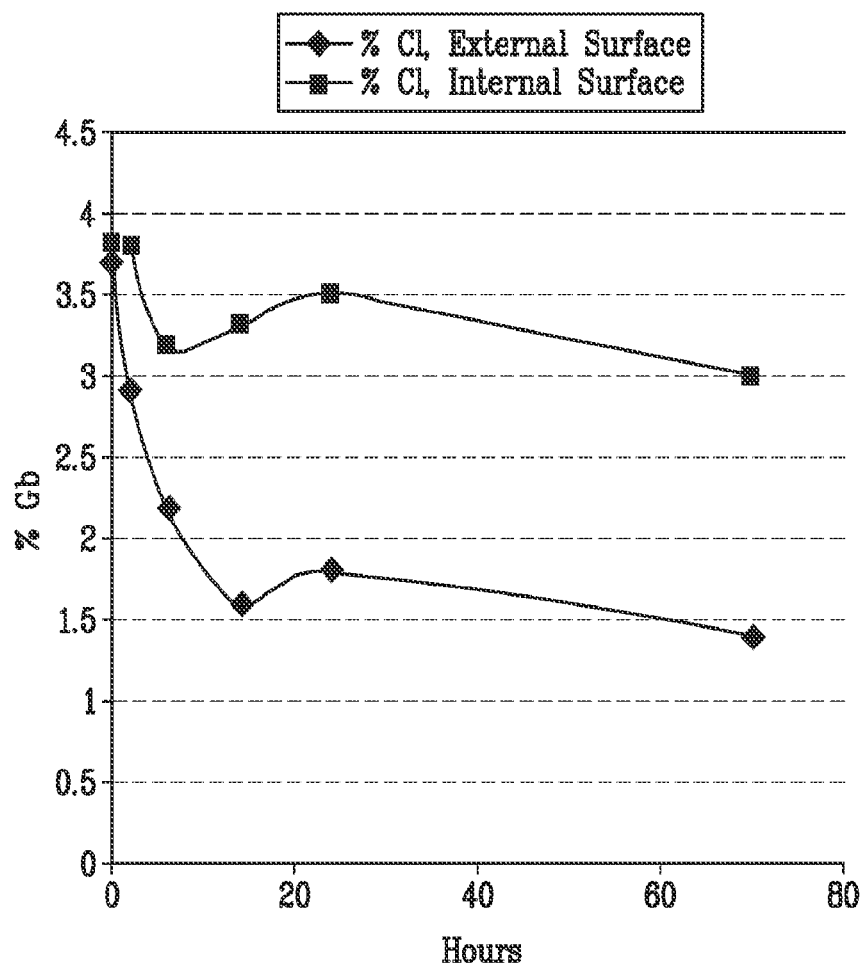
FIG. 5 graphical data of selective hydrolysis.

Selective Hydrolysis of Chloromethylated Polymer,

In a 40 mL glass vial was transferred the chloromethyl polymer 0.52 g, then added 3 mL of toluene to allow the beads to swell for two hours at room temperature, to protect the inside of the beads with organic toluene. Toluene was sucked out with the help of a pipette. Purified water 2.63 mL was added to the polymer and the mixture was heated in an oil bath, provided with a thermocouple at 78° C. for a desired time period with no stirring, occasional shaking was required. This experiment was studied for 2 h, 6 h, 14 h, 24 h and a 70 h time period at 78° C. After the hydrolysis time period was complete, the reaction was cooled to RT (Room Temperature). The aqueous layer was removed via a pipette. The polymer beads were washed with 3 ml of water four times, 3 ml of methanol three times and 2 ml of diethyl ether three times. Let, the polymer air dried for two hours inside the hood, then dried in a high vacuum oven over night at 55° C. The product obtained (0.42 g) in ~85% yield, was analyzed by XPS/ESCA analysis (Table 3 & FIG. 5). FIG. 5 shows a steep drop in the % Cl during the first 14 hours of hydrolysis for the external surface, while the internal content remains relatively constant.

TABLE 3

| Rxn time (h) | % Cl, External Surface | % O, External Surface | % Cl, Internal Surface | % O, Internal Surface |
| --- | --- | --- | --- | --- |
| 0 | 3.7 | 5.5 | 3.8 | 4.6 |
| 2 | 2.9 | 6.1 | 3.8 | 4.7 |
| 6 | 2.2 | 7.3 | 3.2 | 5.4 |
| 14 | 1.6 | 7.5 | 3.3 | 4.7 |
| 24 | 1.8 | 7.5 | 3.5 | 4.6 |
| 70 | 1.4 | 9 | 3.0 | 4.9 |

Example 2

Sorbent Syntheses

In a three neck round bottom flask provided with nitrogen inlet, rubber septum, addition funnel and a magnetic stirrer were transferred sodium hydride (65%), 0.65 g, 0.0176 mol. The oil in sodium hydride was removed by washing two times with 3 ml of dry toluene. The flask was cooled in an ice bath at 0° C. Transferred 3.5 ml of dry DMF via a syringe into sodium hydride, followed by a very slow addition of a solution of Triton-x-100, 12.3 g, 0.0196 mol in 7.0 ml of dry DMF. Lots of gas evolution and frothing was occurred during the addition. Addition time was 35 minutes. After the addition, let stir for another 30 minutes at 0° C. Ice bath was then removed and the reaction was allowed to warm to RT. Solution tuned brown at the end of formation of the anion and all the sodium hydride was disappeared in 2 h at RT.

In a separate 100 ml 3-neck round bottom flask, provided with a nitrogen inlet, rubber septum, addition funnel, mechanical stirrer (glass shaft with a glass blade) and a thermocouple probe were transferred polymer beads, 0.35 g, (chloromethyl group inside the polymer and hydroxyl-methyl outside the polymer), added 7.0 ml of dry DMF via a syringe. To the stirring slurry at 0° C. was added the above prepared anion solution via the addition funnel. This addition was fast in ~5 minutes. Let stir at 0° C. for 10 minutes, warm to RT in ~30 minutes and then heated at 55° C. for 16 h.

Reaction cooled to RT, quenched with ice-water (10 ml), some exotherm 4-5° C. was observed. Water and DMF were removed by vacuum suction. Polymer beads were washed with water 3 times, 0.1N HCl 2 times, 2-propanol 2 times and toluene 2 times. The washed beads were soxhlet with toluene for 16 h. From the beads toluene was washed with methanol 2 times and with diethyl ether 2 times. After air drying for 2 h inside the hood, beads were dried in high vacuum at 55° C. for 16 h.

Figure 6:
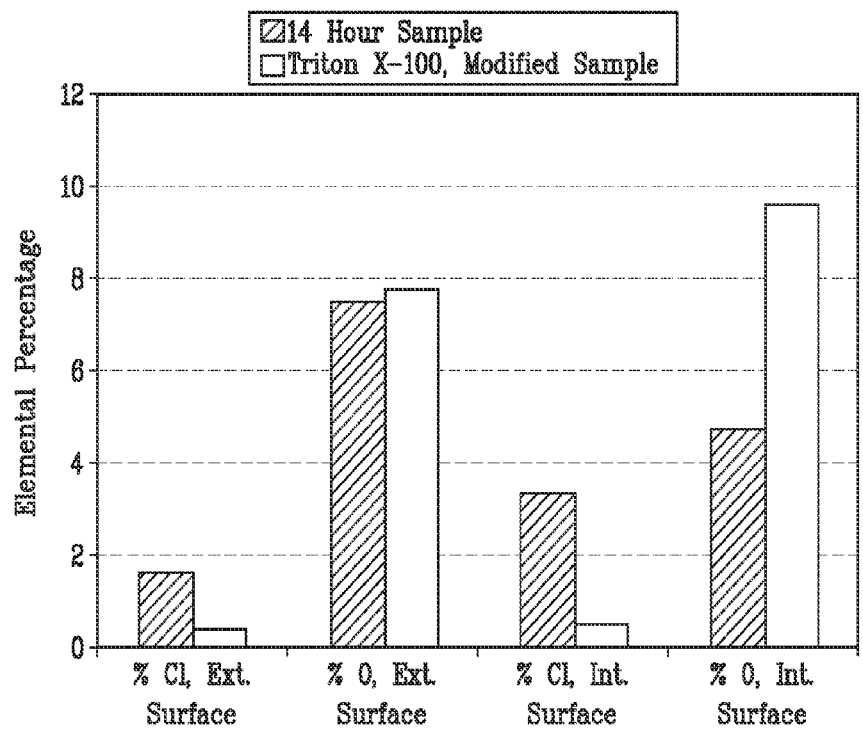
FIG. 6 graphical data of Triton X-100 modification.

The dried beads obtained 0.32 g. A sample was analyzed by XPS/ESCA analysis. The data is shown in Table 5 and graphical analysis is shown in FIG. 6. Triton X-100 has significant oxygen content due to the repeating glycol moieties (n=9–10). The % oxygen on the exterior of the 14 hour hydrolysis sample and the Triton X-100 treated sample are very similar. This indicates minimal modification on the exterior of the beads. The internal oxygen content has increased for the Triton X-100 treated sample indicating selective internal modification.

TABLE 5

| Rxn time (h) | % Cl, External Surface | % O, External Surface | % Cl, Internal Surface | % O, Internal Surface |
| --- | --- | --- | --- | --- |
| 14 Hour Sample | 1.6 | 7.5 | 3.3 | 4.7 |
| Triton X-100, Modified Sample | 0.4 | 7.8 | 0.5 | 9.6 |

Other functional groups besides the chloromethyl group could lend themselves to be utilized via solvent protection in the interior of the porous bead. They include, benzyl aldehydes, carboxylic acids, acid chlorides, amines, epoxides, methyl bromides, benzyl alcohol, sulfonic acids to name just a few.

Example 3

Sorbent Syntheses

The previous approach exploits the lipophilic nature of the CytoSorb (divinylbenzene ethylvinyl benzene copolymer) pore structure. An alternative approach could be would be to take a lipophobic system for the interior and an organic solvent occupying the bead exterior or interstitial space. This organic solvent is non-reactive with a reactive substrate. One example is a carboxylated CytoSorb polymer (Boudenne J L, et al, Polymer International, 51: (2002) 1050-1057.) with an aqueous interior phase and a diethyl ether interstitial phase with the reactive alkylating agent like diazomethane. This would direct the alkylation to the bead exterior. See FIG. 7.

Conversion of Carboxylic Acid to Methyl Ester of Exterior Surface,

Generation of Diazomethane: Sigma Aldrich provided 1 g of N-nitroso-N-methylurea in a 100 ml glass bottle. Sigma's bottle was cooled in an ice bath and added 2.50 ml of diethyl ether. In 40 ml glass vial a 40% potassium hydroxide solution was prepared separately, by dissolving 1.2 g KOH and taking up to 3 ml of water. To the KOH solution was added 7.50 ml of ether and the vial was also cooled in an ice bath.

Pre-cooled KOH/Ether solution was transferred to the Sigma's bottle cooled in an ice bath. A yellow color started to generate immediately in the ether layer (contains diazomethane).

In a separate 40 ml vial was transferred one ml of polymer beads (DVB Polymer/Carboxylic acid). These beads were washed with water 4 times, after the final washing, water was removed via a pipette and the vial was cooled in an ice bath.

Transferred ~2 ml of yellow ether solution to the polymer beads vial, added another few drops, until the yellow color persisted. After 5 minutes the reaction mixture in the ice bath was quenched with ~2-3 ml of 10% acetic acid.

Figure 8:
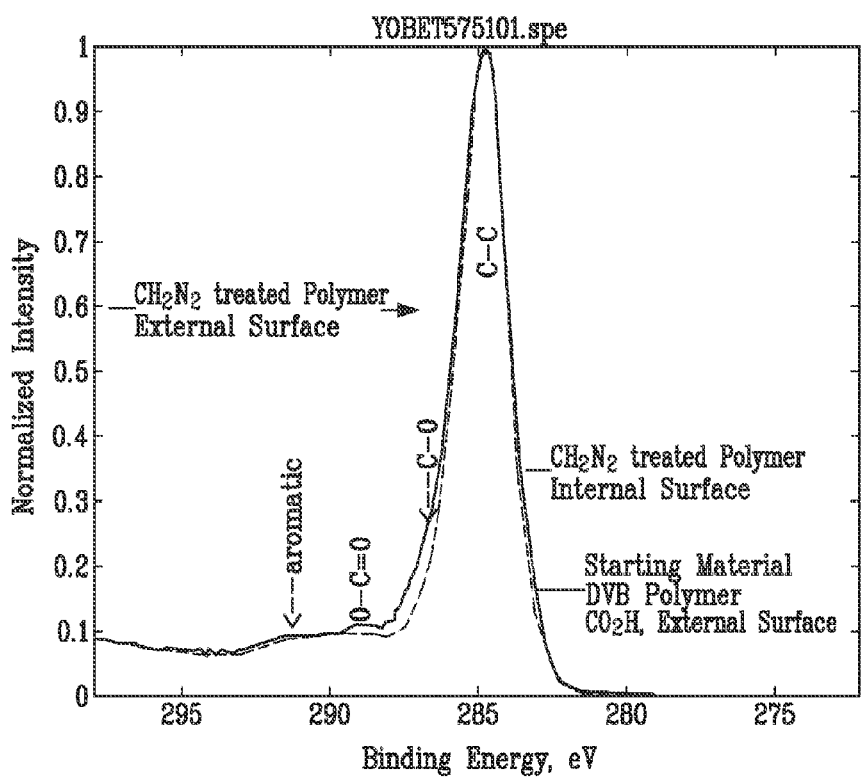
FIG. 8 XPS/ESCA, high resolution analysis overlay of a selective diazomethane reaction.

At the end of reaction (no yellow color), aqueous solution was removed by a pipette. The polymer beads were washed 4 times with water, 2 times with methanol and 2 times with ether. Air dried for 2 h, then in high vacuum at 55° C. A sample was submitted for XPS/ESCA, high resolution analysis (Table 6 & 7, FIG. 8). Data discussed below.

Figure 7:
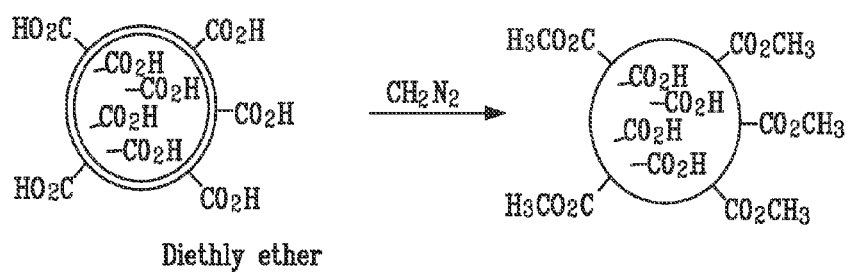
FIG. 7 illustrates use of a carboxylated CytoSorb polymer with an aqueous interior phase and a diethylether interstitial phase with the reactive alkylating agent like diazomethane to direct the alkylation to the bead exterior.

The external surface of $CH_2N_2$ treated Polymer was similar to the DVB Polymer/$CO_2H$ starting material but clearly contained excess C—O when compared with the starting material and the ground version (Internal surface) of $CH_2N_2$ treated Polymer (see FIG. 7). This is demonstrated quantitatively in Table 7 as C—(O,Cl). [Note that this amount exceeds the total C—(O,Cl) for the starting material leading to the conclusion that there may be some C—O present]. The difference in this value is a measure of the amount of methoxy groups on the surface (~4 atom %, 10.8-6.5). This is approximately the same as the total amount of O—C=O suggesting near total conversion of COOH to COO—CH3 on the exterior.

TABLE 6

| Atomic Concentrations (in %) | | | |
| --- | --- | --- | --- |
| Sample | % C | % O | % Cl |
| DVB Polymer, $CO_2H$, External Surface (Starting Material) | 85.1 | 11.8 | 3.2 |
| $CH_2N_2$ treated Polymer, External Surface | 84.7 | 12.0 | 3.3 |
| $CH_2N_2$ treated Polymer, Internal Surface | 86.2 | 10.5 | 3.4 |

Example 4

Sorbent Syntheses

Figure 9:
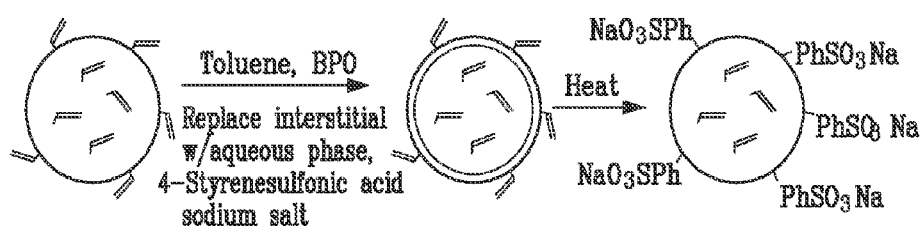

This protecting solvent concept can be extended to free radical grafting chemistry. Divinylbenzene ethylvinyl benzene copolymers have unreacted pendant vinylbenzene groups ranging from 30 to 40% (K. L. Hubbard, J. A. Finch, G. D. Draling, Reactive & Functional Polymers 36 (1998) 17-30). Lipophilic and Lipophobic polymer cores and biphasic conditions can be used to exploit free radical grafting on the interior and exterior of the polymer bead. This can be augmented by the selection of organic soluble and water soluble free radical initiators. An example of this technology is to be found in FIG. 9. The CytoSorb polymer with 4-styrenesulfonic acid sodium salt in an organic solvent (toluene), organic soluble free radical initiator (BPO) is suspended in the bead interior after replacement of the interstitial with an aqueous phase. This allows the system to be initiated thermally directing the graft polymerization to the pore's exterior surface preserving the interior's lipophilic nature.

Reaction of DVB Polymer with Styrenesulfonic Acid Sodium Salt Under Free Radical Conditions, In a 3-neck round bottom flask provided with mechanical stirrer, thermocouple and an air condenser were transferred 10 g, of DVB polymer (swelled in 50 ml of toluene for 16 h) with the help of another 10-15 ml of toluene by adding the rinse to the reaction flask. Benzoyl peroxide 0.04 g, was added to the reaction flask at RT and stirred for 10 minutes. Most of the toluene was removed by vacuum suction. Added a slurry of 4-styrenesulfonic acid sodium salt 4.0 g, and sodium chloride 5.0 g in 50 ml of purified water at RT. Cool the reaction flask in an ice bath (7-9° C.), then added a solution of monosodium phosphate 2.55 g, in 10 ml of water (to keep the reaction pH between 4-5, checked by pH paper). Let, stir at 7-9° C. for 2 h. ice bath removed and reaction mixture was allowed to cool to RT and then heated at 80° C. for 16 h. Reaction mixture was cooled back to RT, aqueous contents were removed by vacuum suction. Added 100 ml of water, warm to 55° C. and water removed by suction. The polymer was washed 4 times with water, 3 times with methanol and soxhlet extracted with methanol overnight. Polymer beads were washed 3 times with diethyl ether, air dried for 2 h in a hood and finally in a high vacuum at 55° C. After drying, 8.5 g of product was obtained. A sample was analyzed by XPS/ESCA analysis. The data is shown in Table

TABLE 7

| | Carbon Chemical State (in Atom % of C) | | | | | | | |
| --- | --- | --- | --- | --- | --- | --- | --- | --- |
| | C—C | | C—(O,Cl) | | O=C—O—(H,R) | | π-π* | |
| Sample | Atom % | eV | Atom % | eV | Atom % | eV | Atom % | eV |
| DVB Polymer, $CO_2H$, External Surface (Starting Material) | 71.8 | 284.8 | 6.5 | 86.6 | 3.9 | 89.2 | 2.8 | 91.5 |
| $CH_2N_2$ treated Polymer, External Surface | 67.7 | 284.8 | 10.8 | 86.7 | 3.6 | 89.1 | 2.5 | 91.5 |
| $CH_2N_2$ treated Polymer, Internal Surface | 72.6 | 284.8 | 7.3 | 86.7 | 3.5 | 89.1 | 2.8 | 91.5 |

Figure 10:
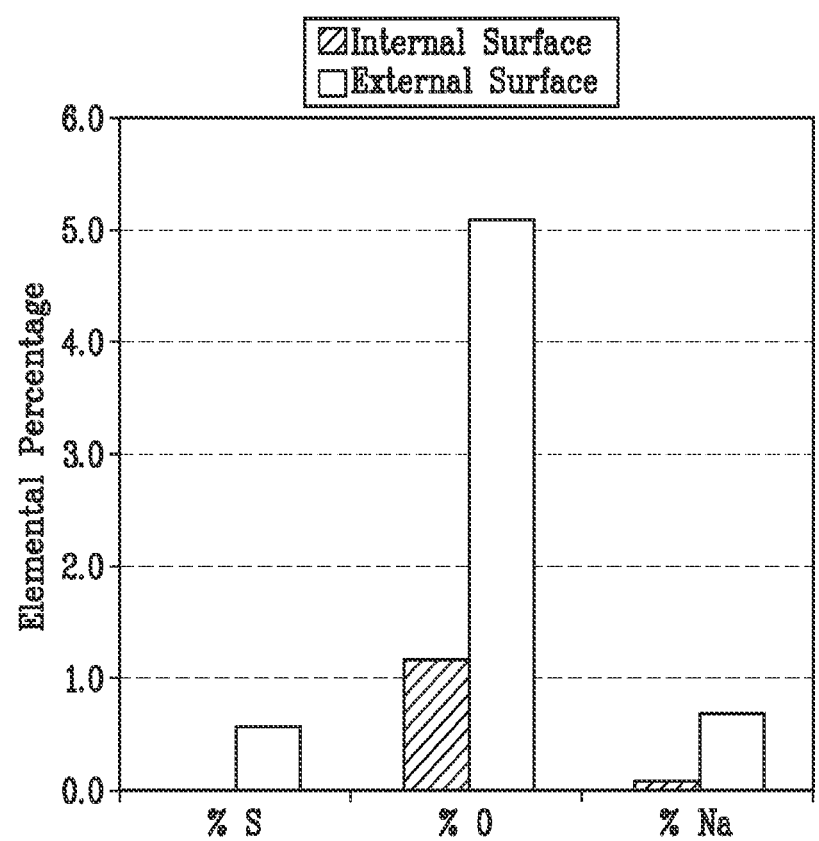

8 and graphical analysis is shown in FIG. 10. The sulfur of the styrene sulfonic acid was only detected on the exterior of the bead.

TABLE 8

| Sample | % S | % O | % Na |
|---|---|---|---|
| Internal Surface | 0.0 | 1.2 | 0.1 |
| External Surface | 0.6 | 5.1 | 0.7 |

Example 5

Sorbent Syntheses

In addition to non-reacting aqueous or organic solvents as protecting media, air or gasses could be utilized to the same manner. One such example is shown below.

Placed two vials each with 1.0 g of Chloromethyl DVB polymer. Set oil bath to 80° C. Added 5 mL of purified water at RT to each vial. Vials placed in oil bath and occasionally shaken by hand. Removed first vial at 10 minutes. Immediately rinsed the sample via vacuum filtration. First washed with cold water, then 2 times methanol, then 3 times diethyl ether. After the ether wash the sample was placed in the oven. Repeated the last 3 steps on the other sample but removed from oil bath after 1 hour. Samples were analyzed by XPS/ESCA analysis. The data is shown in Table 9 and is consistent with higher surface O concentrations and higher interior Cl concentrations.

TABLE 9

| Sample | % O | % Cl |
|---|---|---|
| 10 min, External | 5.7 | 3.0 |
| 10 min, Internal | 3.9 | 3.9 |
| 1 hr, External | 6.0 | 2.6 |
| 1 hr, Internal | 4.0 | 3.6 |

In summary, this protective solvent approach could be applied to polymer beads via:
Free Radical Chemistry
Oxidation/Reduction Chemistry
Lewis acid/Lewis base chemistry

The invention claimed is:

1. A method for the purification of blood, blood product, or physiologic fluid comprising contacting blood, blood product, or physiologic fluid with a porous polymer made by a method comprising:
(a) in a first step, functionalizing the porous polymer on substantially all surfaces; and
(b) in a second step, functionalizing the porous polymer such that a different functional group resides on the external surface and the internal pore surface of the polymer; wherein at least one of said functional groups is selected from aldehyde, carboxylic acid, ether, ester, aromatic, alkyl aromatics, alkyl, wherein said alkyl aromatic group may optionally be substituted with aldehyde, carboxylic acid, halogen, ester or ether; and, wherein said alkyl group may optionally be substituted with aldehyde, carboxylic acid, aromatic, halogen, or ester; said second step comprising:
(i) treating the polymer with a non-aqueous media, aqueous media or gas that is not reactive with the polymer and allowing the non-aqueous media, aqueous media or gas that is not reactive with the polymer to be sorbed into the pores of the polymer;
(ii) removing interstitial non-aqueous media, aqueous media or gas that is not reactive with the polymer, leaving the non-aqueous media, aqueous media or gas that is not reactive with the polymer in the pores;
(iii) suspending the polymer in a solvent comprising Lewis acid, Lewis base, free radical or oxidation/reduction reactants, wherein when said solvent is a non-aqueous solvent, the polymer in step (i) is treated with aqueous media or gas and wherein when said solvent is an aqueous solvent, the polymer is step (i) is treated with non-aqueous media; and
(iv) modifying the external surfaces of the polymer by Lewis acid, Lewis base, free radical or oxidation/reduction reactions;
wherein said porous polymer sorbs one or more of toxins and pathogens from said blood, blood product or physiologic fluid.

2. The method of claim 1, wherein the polymer is in the form of a bead.

3. The method of claim 1, wherein in step (a), substantially all surfaces are initially functionalized via one or more of Lewis acid, Lewis base, free radical or oxidation/reduction reactions.

4. The method of claim 3, wherein:
(i) the external functional groups are selectively modified by treating the porous polymer with a non-aqueous protective media and allowing said non-aqueous protective media to be sorbed in the pores;
(ii) removing interstitial non-aqueous protective media and leaving the non-aqueous protective media in the pores;
(iii) suspending the porous polymer in an aqueous solution; and
(iv) modifying the external surfaces by Lewis acid, Lewis base, free radical or oxidation/reduction reactions in said aqueous solution; said modification leaving the internal surfaces with the initial modification performed in claim 3 substantially unmodified.

5. The method of claim 4, wherein the non-aqueous protective media is an organic solvent or a gas that is not reactive with the polymer.

6. The method of claim 5, wherein
(i) contacting dry polymer with said gas that is not reactive with the polymer;
(ii) suspending said polymer in an aqueous solution; and
(iii) modifying external surfaces of said polymer modified through Lewis acid, Lewis base, free radical or oxidation/reduction reactions in said aqueous solution, leaving the internal surfaces with the initial modification performed in claim 5 substantially unmodified.

7. The method of claim 6, wherein said gas that is not reactive with the polymer is one or more of air, nitrogen or argon.

8. The method of claim 3, wherein the external functional groups are selectively modified by
(i) treating the polymer with an aqueous solution or gas that is not reactive with the polymer and allowing said aqueous solution or gas to be sorbed into the pores;
(ii) removing interstitial aqueous solution or gas, leaving the aqueous solution or gas in the pores;
(iii) suspending the polymer in a reactive organic solvent mix containing Lewis acid; Lewis base, free radical or oxidation/reduction reactants, leaving the internal surfaces with the initial modification performed in claim 3 substantially unmodified.

9. The method of claim 3, wherein the internal functional groups are selectively modified by
(i) sorbing a reactive organic solvent solution containing Lewis acid, Lewis base, free radical or oxidation/reduction reactants into the pores;
(ii) removing interstitial reactive organic solvent solution and leaving the reactive organic solvent in the pores; and
(iii) suspension of the polymer in an aqueous solution leaving the external surfaces with the initial modification performed in claim 3 substantially unmodified.

10. The method of claim 4, wherein the non-aqueous protective media is viscosified to improve retention in the polymer pores.

11. The method of claim 4, wherein the aqueous solution is viscosified to improve retention in the polymer pores.

12. The method of claim 4, wherein the process may be repeated to further derivatize the specific surfaces.

13. A method for the purification of blood, blood product, or physiologic fluid comprising contacting blood, blood product, or physiologic fluid with a polymer comprising a plurality of pores, said pores having external and internal surfaces, said method comprising functionalizing said external surfaces such that functional groups reside on the external pore surfaces; wherein at least one of said functional groups is selected from aldehyde, carboxylic acid, ether, ester, aromatic, alkyl aromatics, alkyl, wherein said alkyl aromatic group may optionally be substituted with aldehyde, carboxylic acid, halogen, ester or ether; and, wherein said alkyl group may optionally be substituted with aldehyde, carboxylic acid, aromatic, halogen, or ester; said method comprising:
(i) treating the polymer with an aqueous solution, non-aqueous protective media, or gas that is not reactive with the polymer and allowing the aqueous solution, non-aqueous protective media or gas that is not reactive with the polymer to be sorbed into the pores of the polymer;
(ii) removing interstitial water, non-aqueous protective media or gas that is not reactive with the polymer, leaving the aqueous solution, non-aqueous protective media or gas that is not reactive with the polymer in the pores;
(iii) suspending the polymer in an organic solvent comprising Lewis acid, Lewis base, free radical or oxidation/reduction reactants; and
(iv) modifying the external surfaces of the polymer by Lewis acid, Lewis base, free radical or oxidation/reduction reactions in said organic solvent;
wherein said porous polymer sorbs one or more of toxins and pathogens from said blood, blood product or physiologic fluid.

14. The method of claim 13, wherein the polymer is in the form of a bead.

15. The method of claim 13, wherein substantially all surfaces are initially functionalized via one or more of Lewis acid, Lewis base, free radical or oxidation/reduction reactions.

16. The method of claim 13, wherein the porous polymer is selectively modified on the external surface by:
(i) treating the polymer with an aqueous solution or gas that is not reactive with the polymer and allowing the aqueous solution or gas that is not reactive with the polymer to be sorbed into the pores of the polymer;
(ii) removing interstitial water or gas that is not reactive with the polymer, leaving the aqueous solution or gas that is not reactive with the polymer in the pores;
(iii) suspending the polymer in a solvent comprising Lewis acid, Lewis base, free radical or oxidation/reduction reactants, wherein when said solvent is a non-aqueous solvent, the polymer is step (i) is treated with aqueous media or gas and wherein when said solvent is an aqueous solvent, the polymer is step (i) is treated with non-aqueous media; and
(iv) modifying the external surfaces of the polymer by Lewis acid, Lewis base, free radical or oxidation/reduction reactions in said non-aqueous solvent.

17. The method of claim 13, wherein the porous polymer is selectively modified on the external surface by
(i) treating with a non-aqueous protective media and said non-aqueous protective media is sorbed into the pores;
(ii) removing interstitial non-aqueous protective media leaving the non-aqueous protective media in the pores;
(iii) suspending the polymer in a reactive aqueous solution; and
(iv) modifying the external surfaces by Lewis acid, Lewis base, free radical or oxidation/reduction reactions in said aqueous solution.

18. The method of claim 17, wherein the non-aqueous protective media is an organic solvent or gas that is not reactive with the polymer.

19. The method of claim 18, wherein
(i) contacting dry polymer with said gas that is not reactive with the polymer;
(ii) suspending said polymer in an aqueous solution; and
(iii) modifying external surfaces of said polymer modified through Lewis acid, Lewis base, free radical or oxidation/reduction reactions in said aqueous solution.

20. The method of claim 19, wherein said gas that is not reactive with the polymer is one or more of air, nitrogen or argon.

21. The method of claim 16, wherein the aqueous solution is viscosified to improve retention in the polymer pores.

22. The method of claim 16, wherein the non-aqueous solvent is viscosified to improve retention in the polymer pores.

23. The method of claim 16, wherein the process may be repeated to further derivatize the specific surfaces.

24. The method claim of 13 where the porous polymer is selectively modified on the internal surface by
(i) treating the polymer with reactive organic solvent mix containing Lewis acid, Lewis base, free radical or oxidation reduction agents and said solvent is sorbed in the pores;
(ii) removing interstitial solvent, leaving the reactive organic solvent mix in the pores; and
(iii) suspending the polymer in an aqueous solution to protect the external surface.

25. The method of claim 24, wherein the organic solvent is viscosified to improve retention in the polymer pores.

26. The method system of claim 24, wherein the process may be repeated to further derivatize the specific surfaces.

* * * * *